United States Patent
Yamanaka et al.

(10) Patent No.: US 9,341,587 B2
(45) Date of Patent: May 17, 2016

(54) ELECTRIC POTENTIAL MEASURING APPARATUS

(71) Applicant: FUJITSU LIMITED, Kawasaki-shi, Kanagawa (JP)

(72) Inventors: Kazunori Yamanaka, Isehara (JP); Kazuaki Kurihara, Atsugi (JP)

(73) Assignee: FUJITSU LIMITED, Kawasaki (JP)

( * ) Notice: Subject to any disclaimer, the term of this patent is extended or adjusted under 35 U.S.C. 154(b) by 422 days.

(21) Appl. No.: 13/913,754

(22) Filed: Jun. 10, 2013

(65) Prior Publication Data

US 2013/0271110 A1    Oct. 17, 2013

Related U.S. Application Data

(63) Continuation of application No. PCT/JP2010/072880, filed on Dec. 20, 2010.

(51) Int. Cl.
| | |
|---|---|
| *G01R 31/02* | (2006.01) |
| *G01N 27/00* | (2006.01) |
| *G01R 25/00* | (2006.01) |
| *G01R 19/00* | (2006.01) |

(Continued)

(52) U.S. Cl.
CPC ............... *G01N 27/00* (2013.01); *A61B 5/053* (2013.01); *G01R 19/0084* (2013.01); *G01R 19/0092* (2013.01); *G01R 23/02* (2013.01); *G01R 25/00* (2013.01); *G01R 29/12* (2013.01); *G01R 21/133* (2013.01); *G01R 31/40* (2013.01)

(58) Field of Classification Search
CPC ........... G01R 19/0084; G01R 19/0092; G01R 23/02; G01R 25/00; G01R 21/133; G01R 31/40

USPC .............. 324/72, 72.5, 76.11–76.83, 119, 149
See application file for complete search history.

(56) References Cited

U.S. PATENT DOCUMENTS

| 5,331,966 A | 7/1994 | Bennett |
|---|---|---|
| 2003/0040305 A1 | 2/2003 | Ng et al. |

(Continued)

FOREIGN PATENT DOCUMENTS

| JP | 62-154795 U | 10/1987 |
|---|---|---|
| JP | 01-209350 A | 8/1989 |

(Continued)

OTHER PUBLICATIONS

International Search Report for International Application No. PCT/JP2010/072880 dated Mar. 22, 2011.

(Continued)

*Primary Examiner* — Huy Q Phan
*Assistant Examiner* — Raul Rios Russo
(74) *Attorney, Agent, or Firm* — Kratz, Quintos & Hanson, LLP

(57) ABSTRACT

An electric potential measuring apparatus includes a detecting unit, a generating unit, and a measuring unit. The detecting unit is provided on a surface of a measurement subject and detects a second signal including a first signal within a first frequency range from the measurement subject. The generating unit generates a fourth signal by averaging a third signal within a second frequency range outside the first frequency range. The measuring unit measures electric potential of the first signal included in the second signal detected by the detecting unit with reference to electric potential of the fourth signal generated by the generating unit.

12 Claims, 18 Drawing Sheets

(51) Int. Cl.
*G01R 23/02* (2006.01)
*G01R 29/12* (2006.01)
*A61B 5/053* (2006.01)
*G01R 21/133* (2006.01)
*G01R 31/40* (2014.01)

(56) References Cited

U.S. PATENT DOCUMENTS

| | | | | |
|---|---|---|---|---|
| 2005/0116700 | A1* | 6/2005 | Yakabe | G01R 27/26 323/370 |
| 2006/0006877 | A1* | 1/2006 | Ichimura | G03G 15/5037 324/458 |
| 2007/0065169 | A1* | 3/2007 | Kandori | G03G 15/5037 399/73 |
| 2008/0311867 | A1* | 12/2008 | Araki | H03D 3/007 455/127.2 |
| 2010/0019779 | A1* | 1/2010 | Kato | G01R 29/12 324/660 |
| 2015/0313496 | A1* | 11/2015 | Connor | A61B 5/0476 600/301 |

FOREIGN PATENT DOCUMENTS

| | | |
|---|---|---|
| JP | 06-90914 A | 4/1994 |
| JP | 2655204 B2 | 5/1997 |
| JP | 2002-111602 A1 | 4/2002 |
| JP | 2004-500217 A | 1/2004 |
| JP | 2008-86390 A1 | 4/2008 |
| JP | 2009-118999 A1 | 6/2009 |
| JP | 2010-12161 A1 | 1/2010 |
| JP | 2010-22623 A1 | 2/2010 |

OTHER PUBLICATIONS

Reconsideration Report dated May 22, 2015 for corresponding Japanese Patent Application No. 2012-549499 retrieved on Jun. 2, 2015. Translation of relevant part: p. 1 line 8 to line 27.
Office Action mailed Mar. 15, 2016 for corresponding Japanese Application No. 2012-549499, with translation of relevant part: p. 1 line 24 to p. 5 line 10.

* cited by examiner

ELECTRIC POTENTIAL MEASURING APPARATUS

CROSS-REFERENCE TO RELATED APPLICATION

This application is a continuation application of International Application PCT/JP2010/072880 filed on Dec. 20, 2010 which designated the U.S., the entire contents of which are incorporated herein by reference.

FIELD

The embodiments discussed herein are related to an electric potential measuring apparatus.

BACKGROUND

There are known methods and apparatuses for measuring electric potentials of biosignals in plants and animals (including humans), low-frequency signals on the ground or similar environmental objects, and other signals of various subjects. Another known technique permits an information processing terminal such as a personal computer (PC) to collect electric potential measurement data from those measurement apparatuses via wired or wireless communication links.

For example, there is a known technique to provide electrodes on clothes a person who is a test subject wears, and to detect biological signals of the test subject by using the electrodes; and another known technique to externally send and collect signals detected by a medical device implanted in a human body. Moreover, there is another known technique to paste, for example, three external electrodes (a positive electrode, a negative electrode, and an indifferent electrode), which are coupled to the main body of an electrocardiograph via wiring (leads), to a test subject's body surface and measure an electrocardiogram. Still another known technique is to measure an electrocardiographic waveform of a test subject in a measurement posture in contact with three exposed electrodes (a positive electrode, a negative electrode, and an indifferent electrode) which are provided at specified positions on a surface of an electrocardiograph.

The electric potential measurement using electric potential measurement apparatuses like those described above is performed by detecting signals at a plurality of measurement points on the subject. An electric potential observed at one of those points is used as a reference electric potential for measurement of signals at other points.

Japanese Laid-open Patent Publication No. 2010-22623
Japanese Patent No. 2655204
Japanese Laid-open Patent Publication No. 2009-118999
Japanese Laid-open Patent Publication No. 2010-12161

A type of electric potential measuring apparatus, whose electrodes for detecting signals at respective measurement points, including a measurement point for the reference electric potential, are coupled to the main body of the apparatus via wiring in order to measure electric potentials at a plurality of measurement points, has a problem of requiring burdensome work to connect wires. The wiring between the electrodes and the main body of the apparatus may be eliminated with respect to the measurement points, except the measurement point for the reference electric potential, for example, by wirelessly transmitting measurement data. However, if the wiring between the electrode for detecting a reference signal to obtain the reference electric potential and the main body of the apparatus is eliminated, the signal may be disturbed and the reference electric potential may fluctuate, and accordingly the electric potential may not be properly measured.

Another known apparatus is a portable-type electric potential measuring apparatus in which a plurality of exposed electrodes, including an electrode for detecting a reference signal, is provided on a surface of the main body of the apparatus, and which detects signals without using wiring between measurement points and the main body of the apparatus. The above-mentioned problem of requiring burdensome work for connecting wires does not occur in the case of such a portable-type electric potential measuring apparatus. However, with such an electric potential measuring apparatus, the electrode for detecting the reference signal, among the plurality of electrodes exposed on the main body of the apparatus, is located at a position distant from other signal detecting electrodes along a signal propagation path in the measurement subject. As a result, the arrangement of the electrodes on the main body of the apparatus is mostly fixed in a certain pattern, thereby possibly causing problems such as, for example, shape limitations in measurement subjects which may be measured, positional limitations in the measurement points on the relevant measurement subject, and limited type(s) of measurement subjects which may be measured.

The conventional electric potential measuring apparatuses as described above use one of signals, which are similarly detected at the plurality of measurement points, as the reference signal and use other signals as target signals whose electric potential is to be measured. When the electrodes, which are placed at the plurality of measurement points, and the main body of the relevant apparatus are connected via wiring in such an electric potential measuring apparatus, electric potentials of the measurement subject may not be sometimes easily measured. Moreover, in the case of an electric potential measuring apparatus which does not require wiring, the reference electric potential may be disturbed and the electric potential of the target signal whose electric potential is to be measured may not be measured properly. Furthermore, the electrode for detecting the reference signal is located at a position distant from the electrodes for detecting the signals whose electric potential is to be measured, along the signal propagation path in the measurement subject. So, targets on which the electric potential measuring apparatus is to be used may be limited.

SUMMARY

According to one aspect of the embodiments, there is provided an electric potential measuring apparatus including: a detecting unit configured to detect a second signal including a first signal from a measurement subject by contacting a surface of the measurement subject, the first signal being an electric potential measurement target signal within a first frequency range, which propagates through the measurement subject; a generating unit configured to generate a fourth signal by averaging a third signal within a second frequency range which is different from the first frequency range; and a measuring unit for measuring electric potential of the first signal with reference to electric potential of the fourth signal.

The object and advantages of the invention will be realized and attained by means of the elements and combinations particularly pointed out in the claims.

It is to be understood that both the foregoing general description and the following detailed description are exemplary and explanatory and are not restrictive of the invention.

DESCRIPTION OF EMBODIMENTS

Figure 1:
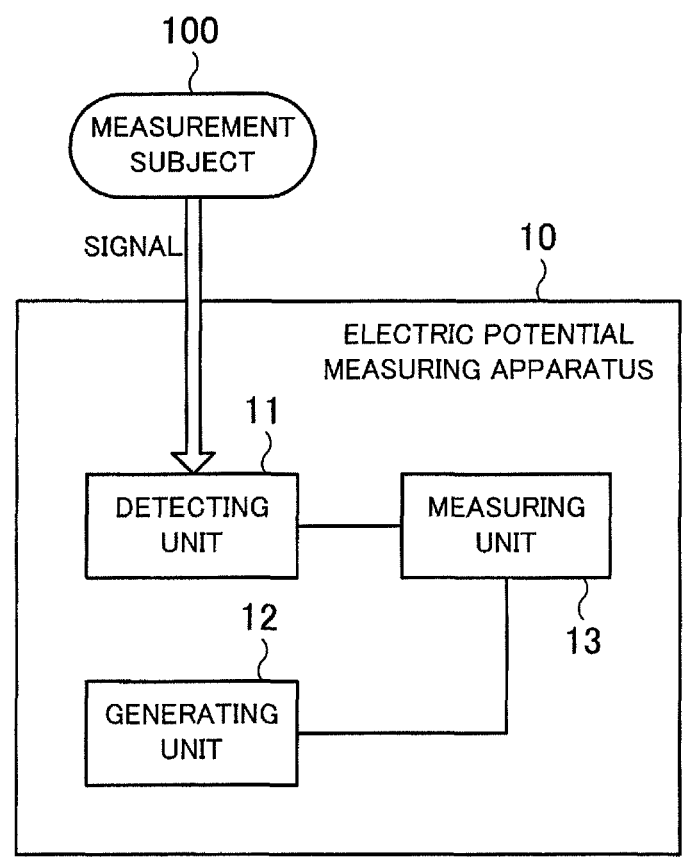
FIG. 1 illustrates a configuration example for an electric potential measuring apparatus.

FIG. 1 illustrates a configuration example for an electric potential measuring apparatus.

An electric potential measuring apparatus 10 depicted in FIG. 1 includes a detecting unit 11, a generating unit 12, and a measuring unit 13.

The detecting unit 11 detects signals from a measurement subject 100. The detecting unit 11 is made to come into contact with the measurement subject 100 and detects the signals directly from the measurement subject 100.

Various examples of the measurement subject 100 include ground surfaces, machinery and equipment as well as living organisms such as animals and plants. A distribution of electric potentials may exist in such a measurement subject 100 because, for example, low-frequency signals and long-term fluctuating waves propagate through the measurement subject 100. The detecting unit 11 is made to come into contact with a specified measurement point on the measurement subject 100 and detects a signal, which propagates though the measurement subject 100, at that measurement point.

The generating unit 12 generates a reference signal indicating reference electric potential, which is used to measure electric potential at the measurement point from the signal detected by the detecting unit 11. To this end, the generating unit 12 uses an auxiliary signal whose specified frequency range is different from (e.g., higher than) signals originating in the measurement subject 100. In other words, this auxiliary signal does not originate from the measurement subject 100. The generating unit 12 produces a reference signal by averaging the auxiliary signal.

The electric potential measuring apparatus 10 is capable of producing an auxiliary signal having a specified frequency range, which is used to generate the reference signal. For example, the auxiliary signal is produced in the electric potential measuring apparatus 10 by using an oscillator circuit or a noise generating circuit.

The generating unit 12 uses, for example, directly the auxiliary signal produced in the electric potential measuring apparatus 10 and generates the reference signal by averaging the auxiliary signal.

Alternatively, the auxiliary signal, which is produced in the electric potential measuring apparatus 10, is supplied to the measurement subject 100. In this case, the detecting unit 11 detects a signal including both the supplied signal of the specified frequency range and the signal which originates in the measurement subject 100. Of the signals detected by the detecting unit 11 in this manner, the generating unit 12 uses and averages the auxiliary signal, which is supplied from the electric potential measuring apparatus 10, and thereby generates the reference signal.

The measuring unit 13 measures electric potential at a measurement point from the signal detected by the detecting unit 11 with reference to the reference signal generated by the generating unit 12.

Now, when the detecting unit 11 detects only the signal which originates in the measurement subject 100, the measuring unit 13 measures the electric potential of the signal with reference to the electric potential of the reference signal generated by the generating unit 12.

Furthermore, the detecting unit 11 may detect a signal including the auxiliary signal supplied from the electric potential measuring apparatus 10 to the measurement subject 100, and the signal which originates in the measurement subject 100, as described earlier. In this case, the measuring unit 13 selects the signal which originates in the measurement subject 100, from the signal detected by the detecting unit 11, and measures the electric potential of the selected signal with reference to the electric potential of the reference signal generated by the generating unit 12.

The electric potential measuring apparatus 10 may include one or more modules, each implementing the above-described detecting unit 11, generating unit 12, and measuring unit 13. For example, these modules are placed on a measurement subject 100 to collect data from different measurement points, thus obtaining a distribution of electric potentials on that measurement subject 100.

It is possible to provide, for example, each module with a mechanism for producing the auxiliary signal, which is to be used when the generating unit 12 generates the reference signal. As a result, it is possible to generate the reference signal in each module and measure the electric potential of a signal detected at the relevant measurement point.

Furthermore, a mechanism for producing and supplying the relevant auxiliary signal may be provided in, for example, each module including the detecting unit 11, the generating unit 12, and the measuring unit 13, or one of such modules in order to supply the auxiliary signal to the measurement subject 100. Alternatively, a module including such a mechanism may be provided separately and used with each module described above.

With the electric potential measuring apparatus 10, it is possible to measure the electric potential of the measurement subject 100 without providing wiring between the measurement subject 100 and the electric potential measuring apparatus 10 by making the electric potential measuring apparatus 10 (the module(s) included in the electric potential measuring apparatus 10) come into contact with the measurement subject 100. Furthermore, it is also possible to place the electric potential measuring apparatus 10 (the module(s) included in the electric potential measuring apparatus 10) at each of arbitrary measurement points on the measurement subject 100 and thereby obtain various distributions of electric potentials in the measurement subject 100. The electric potential measuring apparatus 10 does not use any one of the measured signals as the reference signal, but generates the reference signal from the auxiliary signal outside a frequency range of the measurement target signal (the signal which originates in the measurement subject 100) and measures the electric potential of the measurement target signal by using the electric potential of the generated signal as the reference electric potential.

The electric potential measuring apparatus will be explained in more detail.

Firstly, a first embodiment will be explained.

Now an explanation will be given about an electric potential measuring apparatus including a module which produces a signal to be used to generate the reference signal and supplies it to the measurement subject (signal producing module), and a module which detects a signal from the measurement subject and measures the electric potential at a measurement point (electric potential measuring module).

Figure 2:
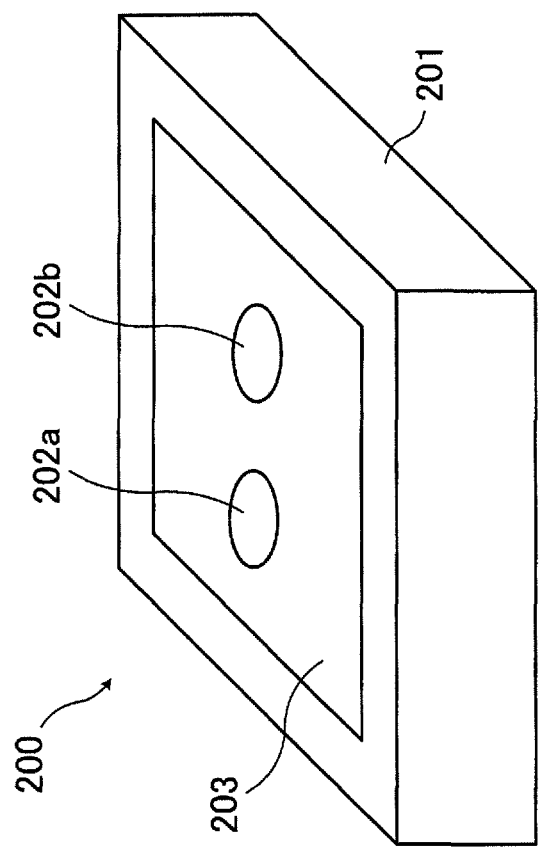
FIG. 2 illustrates an example of a signal producing module according to a first embodiment.

FIG. 2 illustrates an example of the signal producing module according to the first embodiment.

A signal producing module 200 depicted in FIG. 2 includes a housing 201 and electrodes 202a and 202b for supplying signals. The housing 201 is formed from, for example, a high-resistance and electrically-conductive material. At least a mechanism for producing the auxiliary signal which is used to generate the reference signal (producing unit) is placed in the housing 201. It is possible to output the signal, which is produced by the producing unit placed inside the housing 201, from the electrodes 202a and 202b exposed on a surface of the housing 201 to outside the housing 201. An insulative adhesive material 203 is provided on the surface of the housing 201 where the electrodes 202a and 202b are mounted, so that the electrodes 202a and 202b are exposed.

The electric potential measuring apparatus according to the first embodiment includes, for example, one signal producing module 200.

Figure 3:
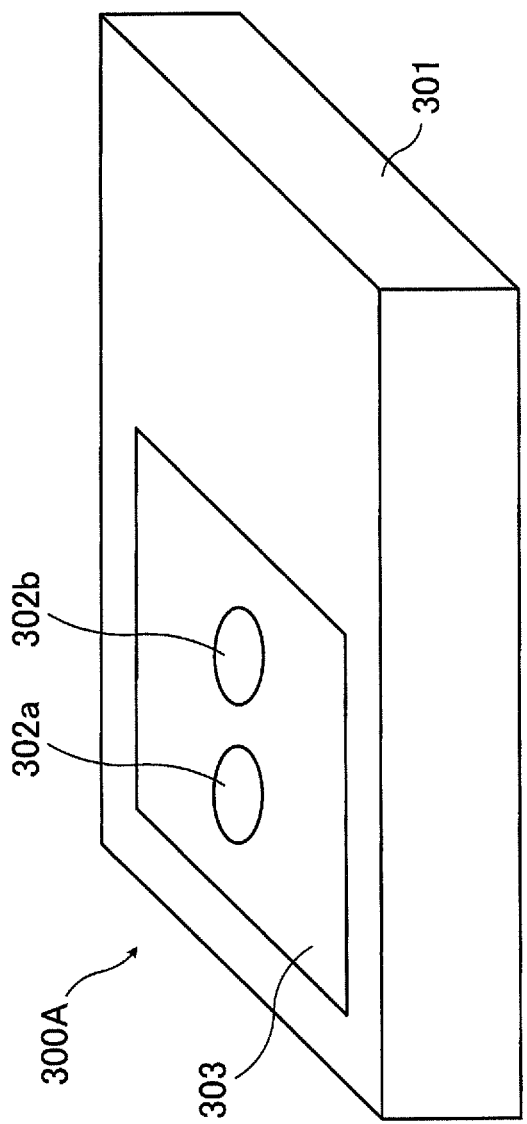
FIG. 3 illustrates an example of an electric potential measuring module according to the first embodiment.

FIG. 3 illustrates an example of an electric potential measuring module according to the first embodiment.

An electric potential measuring module 300A depicted in FIG. 3 includes a housing 301 and electrodes 302a and 302b for detecting signals. The housing 301 is formed from, for example, a high-resistance and electrically-conductive material. At least the generating unit to generate the reference signal and the measuring unit to measure electric potentials are placed inside the housing 301. The generating unit placed inside the housing 301 generates the reference signal and the measuring unit measures the electric potentials by using the reference signal and signals detected by the electrodes 302a and 302b. An insulative adhesive material 303 is provided on the surface of the housing 301 where the electrodes 302a and 302b are mounted, so that the electrodes 302a and 302b are exposed.

The electric potential measuring apparatus according to the first embodiment includes, for example, a plurality of such electric potential measuring modules 300A.

Figure 4:
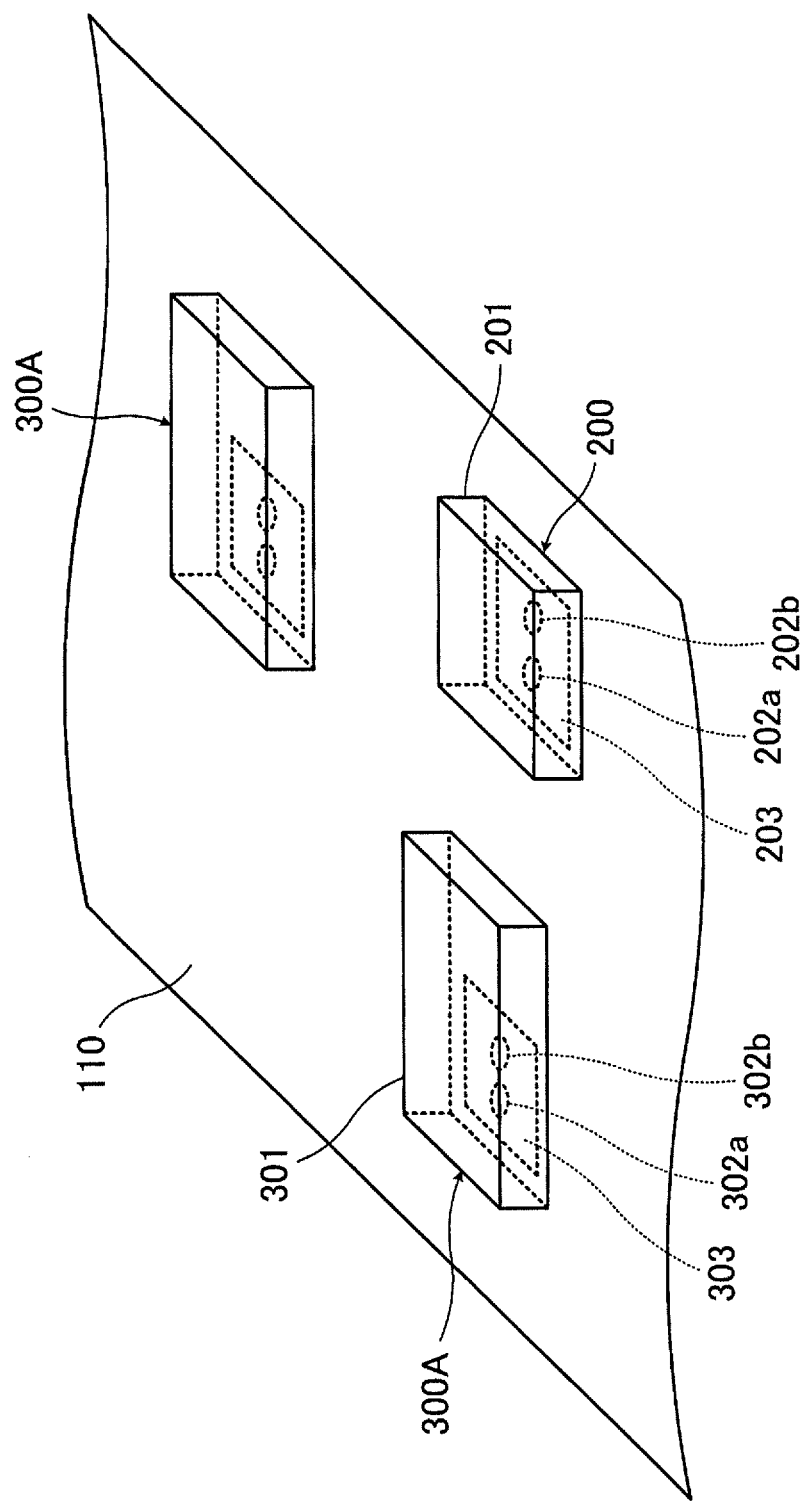
FIG. 4 illustrates an example of a state where the signal producing module and electric potential measuring modules according to the first embodiment are placed on a measurement subject.

FIG. 4 illustrates an example of a state where the signal producing module and the electric potential measuring modules according to the first embodiment are placed on a measurement subject.

FIG. 4 illustrates an example of a measurement subject 110 having a curved surface. Incidentally, the measurement subject 110 may have a flat surface. Various examples of the measurement subject 110 include living organisms, ground surfaces, machinery, and equipment.

FIG. 4 illustrates a state where one signal producing module 200 as depicted in FIG. 2 and two electric potential measuring modules 300A as depicted in FIG. 3 are placed on the surface of the measurement subject 110. Considering a human body as an example of the measurement subject 110, an electric current flows through the surface of the human body. Therefore, it is possible to deliver a signal produced by the signal producing module 200 to the electric potential measuring module 300A via the surface of the human body.

The signal producing module 200 is placed so that its surface where the electrodes 202a and 202b are mounted faces the surface of the measurement subject 110. The signal producing module 200 is adhesively attached to the surface of the measurement subject 110 via the adhesive material 203 provided on the surface where the electrodes 202a and 202b are mounted. Accordingly, the electrodes 202a and 202b come into contact with the surface of the measurement subject 110 and the signal produced by the signal producing module 200 is supplied from the electrodes 202a and 202b to the measurement subject 110.

Similarly, the electric potential measuring module 300A is also placed on the surface of the measurement subject 110 so that its surface where the electrodes 302a and 302b are mounted faces the surface of the measurement subject 110. The electric potential measuring module 300A is adhesively attached to the surface of the measurement subject 110 via the adhesive material 303 provided on the surface where the electrodes 302a and 302b are mounted. Accordingly, the electrodes 302a and 302b come into contact with the surface of the measurement subject 110 and the signal propagating through the measurement subject 110 is detected by the electrodes 302a and 302b. In a case of this electric potential measuring apparatus according to the first embodiment, a signal including both the signal supplied from the signal producing module 200 and the signal which originates in the measurement subject 100 is detected by the electrodes 302a and 302b.

Next, the configuration of the signal producing module 200 and the electric potential measuring module 300A will be explained in more detail.

Figure 5:
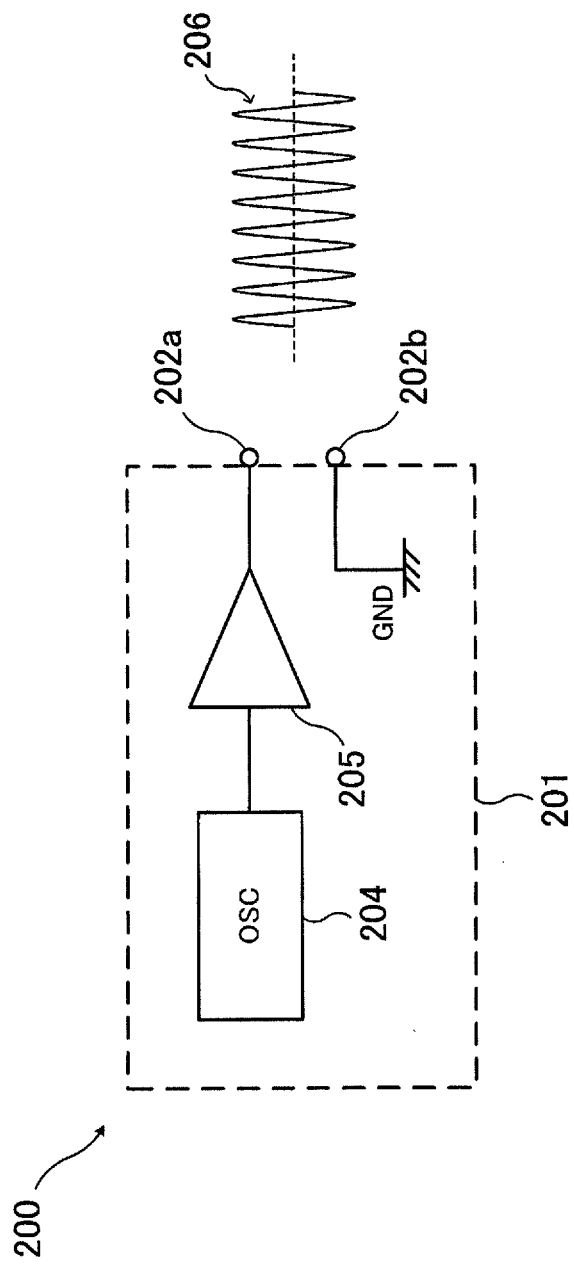
FIG. 5 illustrates a configuration example for the signal producing module according to the first embodiment.

FIG. 5 illustrates a configuration example for the signal producing module according to the first embodiment.

The signal producing module 200 includes an oscillator (OSC) 204 as the producing unit, which produces the auxiliary signal, in the housing 201 as depicted in FIG. 5. The signal oscillated by the oscillator 204 is amplified by an amplifier 205 and the amplified signal 206 is output from the electrode 202a. The other electrode 202b serves as a ground (GND). When the signal producing module 200 is placed on the measurement subject 110, the signal 206 produced by the signal producing module 200 is supplied and propagated to the measurement subject 110.

The frequency of the signal oscillated by the oscillator 204 is set to a value within a frequency range outside the frequency range of the signal which originates in the measurement subject 110. For example, when the frequency range of the signal which originates in the measurement subject 110 is up to about several tens of Hz, a value of frequencies on the order of kHz to MHz is applied as the frequency of the signal oscillated by the oscillator 204. For example, the oscillator 204 which oscillates a 1.2 MHz signal is used for the signal producing module 200.

Incidentally, when the frequency of the signal oscillated by the oscillator 204 is higher, stable waveforms are easily supplied to the plurality of electric potential measuring modules 300A placed on the same measurement subject 110 and this is relatively effective for subsequent processing such as equalization. It is also possible to apply even higher frequencies on the order of GHz, depending on the form of the measurement subject 110.

Figure 6:
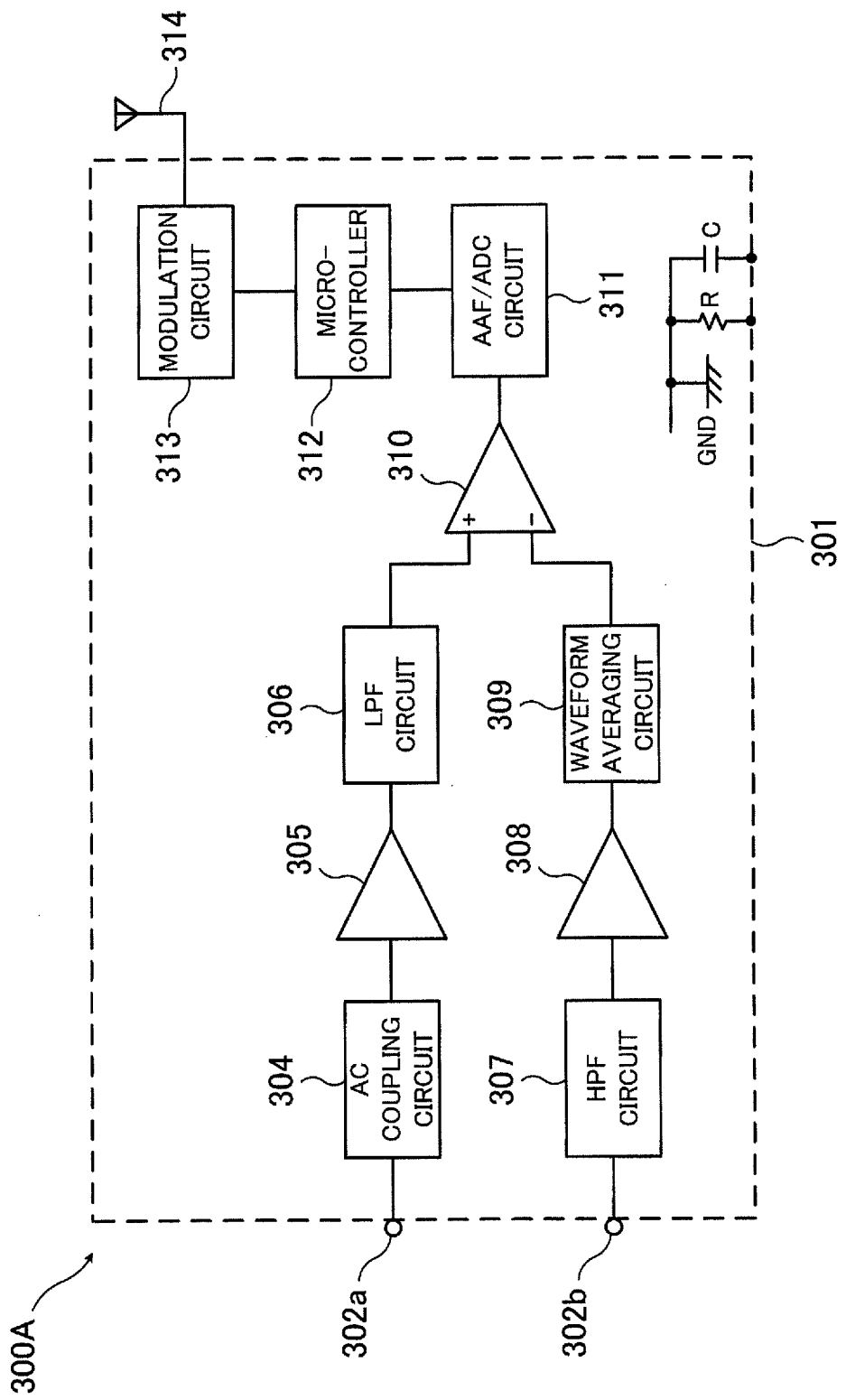
FIG. 6 illustrates a configuration example for the electric potential measuring module according to the first embodiment.

FIG. 6 illustrates a configuration example for the electric potential measuring module according to the first embodiment.

The electric potential measuring module 300A includes an AC coupling circuit 304, an amplifier 305, and a low-pass filter (LPF) circuit 306, which are coupled to one electrode 302a as depicted in FIG. 6.

In this circumstance, the AC coupling circuit 304 uses a high-pass filter (HPF) circuit, which is set to a specified cut-off frequency fc, to remove the direct current (DC) component from the signal detected by the electrode 302a and allows alternating current (AC) components to pass. The amplifier 305 amplifies the output signal from the AC coupling circuit 304. Of the output signal from the amplifier 305, the LPF circuit 306 allows signal components of frequencies lower than the specified cut-off frequency fc to pass and cuts off signal components of frequencies higher than the cut-off frequency fc.

The electric potential measuring module 300A includes an HPF circuit 307, an amplifier 308, and a waveform averaging circuit 309 which are coupled to the other electrode 302b as depicted in FIG. 6.

Of the signal detected by the electrode 302b in this circumstance, the HPF circuit 307 allows signal components of frequencies higher than the specified cut-off frequency fc to pass and cuts off signal components of frequencies lower than the cut-off frequency fc. The amplifier 308 amplifies the output signal from the HPF circuit 307. The waveform averaging circuit 309 averages (or smoothes) the waveform of the output signal from the amplifier 305.

The electric potential measuring module 300A includes a differential amplifier 310 to which the output signal from the LPF circuit 306 and the output signal from the waveform averaging circuit 309 are input, and which amplifies the difference between them.

Furthermore, the electric potential measuring module 300A includes an AAF/ADC circuit 311, which is a circuit including an Antialiasing filter (AAF) and an A/D converter (ADC), a microcontroller 312, a modulation circuit 313, and an antenna 314.

In this circumstance, the AAF/ADC circuit 311 converts an analog signal, which is output from the differential amplifier 310, to a digital signal at the ADC circuit via the AAF circuit. The microcontroller 312 executes specified control processing on the digital signal converted by the AAF/ADC circuit 311. The modulation circuit 313 executes modulation processing (such as phase modulation and frequency modulation) on the output signal from the microcontroller 312, thereby generating a signal within a specified frequency band. The antenna 314 emits the signal generated by the modulation circuit 313 as radio waves.

Each circuit of the electric potential measuring module 300A is coupled to the ground (GND). In this example, the housing 301 (including resistance component R and capacitor component C) is used as the ground.

Next, the measurement of electric potentials by using the electric potential measuring apparatus including the signal producing module 200 and electric potential measuring module 300A which have the above-described configuration will be explained.

When measuring electric potential, the signal producing module 200 and the electric potential measuring module 300A are firstly placed at specified positions on the measurement subject 110 as depicted in FIG. 4.

For example, a 1.2 MHz signal oscillated by the oscillator 204 as depicted in FIG. 5 is amplified by the amplifier 205 and then supplied via the electrodes 202a and 202b from the signal producing module 200 to the measurement subject 110.

With the electric potential measuring module 300A, the electrodes 302a and 302b detect a signal which propagates through the measurement subject 110. In the example indicated in this first embodiment, a signal including the signal, which originates in the measurement subject 110, and the signal which is supplied from the signal producing module 200 and propagates through the measurement subject 110, is detected at each of the electrodes 302a and 302b.

Regarding the signal detected by the electrode 302a, its DC component is removed by the AC coupling circuit 304. The cut-off frequency fc at the AC coupling circuit 304 is set to a frequency lower than the frequency of a measurement target signal from the measurement subject 110, that is, the frequency of the signal which originates in the measurement subject 110. For example, when the frequency of the measurement target signal from the measurement subject 110 is within a frequency range that does not exceed 20 Hz, the cut-off frequency fc at the AC coupling circuit 304 is set to 0.1 Hz.

The output signal from the AC coupling circuit 304 is amplified by the amplifier 305 and then signal components of frequencies higher than the specified cut-off frequency fc are cut off by the LPF circuit 306. The cut-off frequency fc of the LPF circuit 306 is set to a frequency higher than the frequency of the measurement target signal from the measurement subject 110 (the signal which originates in the measurement subject 110). For example, when the frequency of the measurement target signal from the measurement subject 110 is within the frequency range which does not exceed 20 Hz as described above, the cut-off frequency fc of the LPF circuit 306 is set to 20 Hz.

The output signal from the LPF circuit 306 is input to the differential amplifier 310. Specifically speaking, the signal which originates in the measurement subject 110 and which is obtained by cutting the signal supplied from the signal producing module 200 (1.2 MHz frequency in this example) from of the signal detected by the electrode 302a is input to the differential amplifier 310.

Meanwhile, regarding the signal detected by the electrode 302b, signal components of frequencies lower than the specified cut-off frequency fc are cut off by the HPF circuit 307. The cut-off frequency fc of the HPF circuit 307 is set to a frequency higher than the frequency of the measurement target signal from the measurement subject 110 (the signal which originates in the measurement subject 110) and lower than the frequency of the signal supplied from the signal producing module 200. For example, when the frequency of the measurement target signal from the measurement subject 110 is within a frequency range that does not exceed 20 Hz and the frequency of the signal supplied from the signal producing module 200 is 1.2 MHz, the cut-off frequency fc of the HPF circuit 307 is set to 1 MHz.

Incidentally, an LPF circuit which is set to a cut-off frequency fc (for example, 0.1 Hz) lower than the frequency of the measurement target signal from the measurement subject 110 (the signal which originates in the measurement subject 110) may be provided between the electrode 302b and the amplifier 308.

The output signal from the HPF circuit 307 is input to the amplifier 308. Specifically speaking, the signal which is supplied from the signal producing module 200 and obtained by cutting the signal, which originates in the measurement subject 110, from the signal detected by the electrode 302b is input to the amplifier 308.

The signal amplified by the amplifier 308 is input to the waveform averaging circuit 309. The waveform averaging circuit 309 may be implemented by using a Miller integrator.

Figure 7:
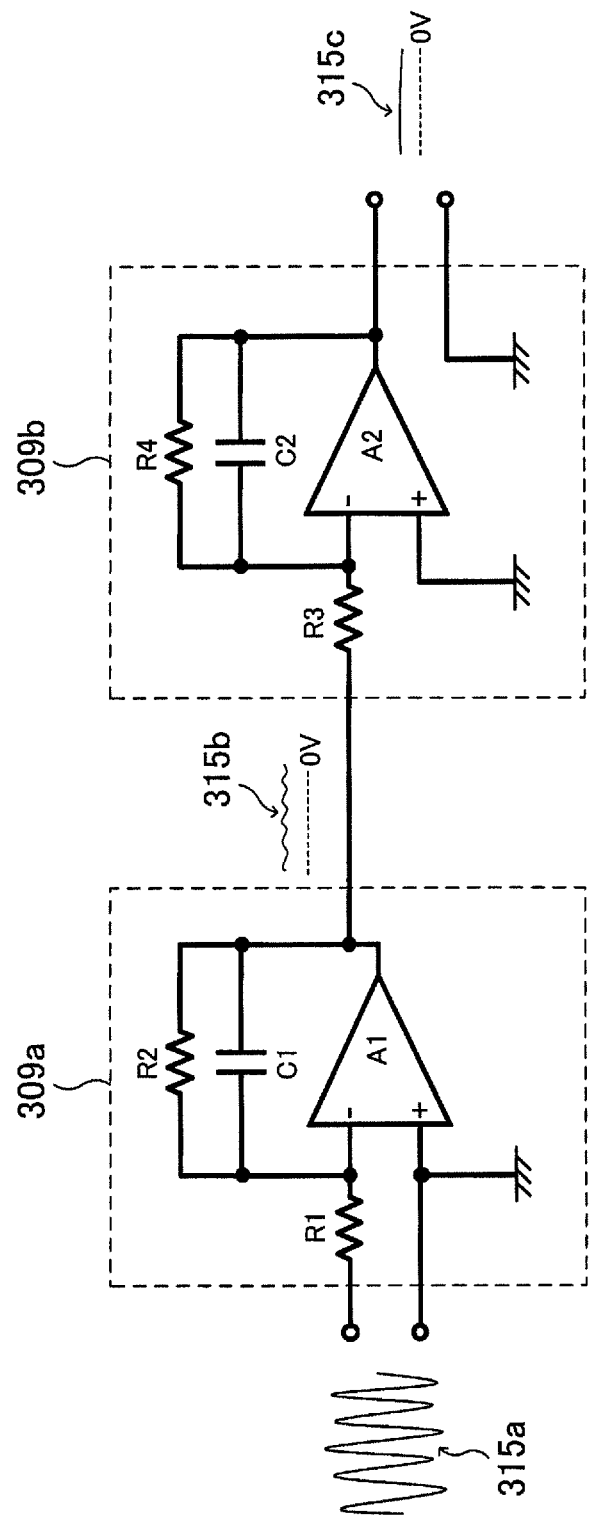
FIG. 7 illustrates a configuration example for a waveform averaging circuit.

FIG. 7 illustrates a configuration example for a waveform averaging circuit.

FIG. 7 illustrates the waveform averaging circuit 309 including Miller integrators 309a and 309b which are connected in multiple stages (two stages in this example).

Respective components (amplifiers A1 and A2, capacitors C1 and C2, and resistors R1 to R4) of the first-stage Miller integrator 309a and the second-stage Miller integrator 309b are set so that their cut-off frequencies fc become different.

A signal 315a amplified by the amplifier 308 depicted in FIG. 6 is firstly input to and averaged by the first-stage Miller integrator 309a of this waveform averaging circuit 309. A signal 315b which is output from the Miller integrator 309a is then input to and further averaged by the second-stage Miller integrator 309b, thereby outputting a signal 315c. The thus-averaged signal 315c is input to the differential amplifier 310 depicted in FIG. 6. This signal 315c becomes the reference signal.

Two types of signals, that is, a signal of a relatively low frequency which originates in the measurement subject 110 and a signal with a relatively high frequency (reference signal) which is supplied from the signal producing module 200 and then averaged are input to the differential amplifier 310 depicted in FIG. 6. Then, the differential amplifier 310 amplifies the difference between these two types of signals. Specifically speaking, the electric potential of the signal which has passed through the LPF circuit 306 (the signal which originates in the measurement subject 110) is obtained with reference to the electric potential of the signal averaged by the waveform averaging circuit 309 (the reference signal); and the thus-obtained electric potential is amplified and output from the differential amplifier 310.

The output signal from the differential amplifier 310 is converted into a digital signal by the AAF/ADC circuit 311; and the digital signal is processed by the microcontroller 312 and then input to the modulation circuit 313; and the signal generated by the modulation circuit 313 is output from the antenna 314.

When a plurality of electric potential measuring modules 300A are placed on the measurement subject 110, the above-described processing is executed by each electric potential measuring module 300A.

The signal output from the antenna 314 is collected by, for example, an information processing terminal such as a personal computer (PC) equipped with a signal receiving function.

Figure 8:
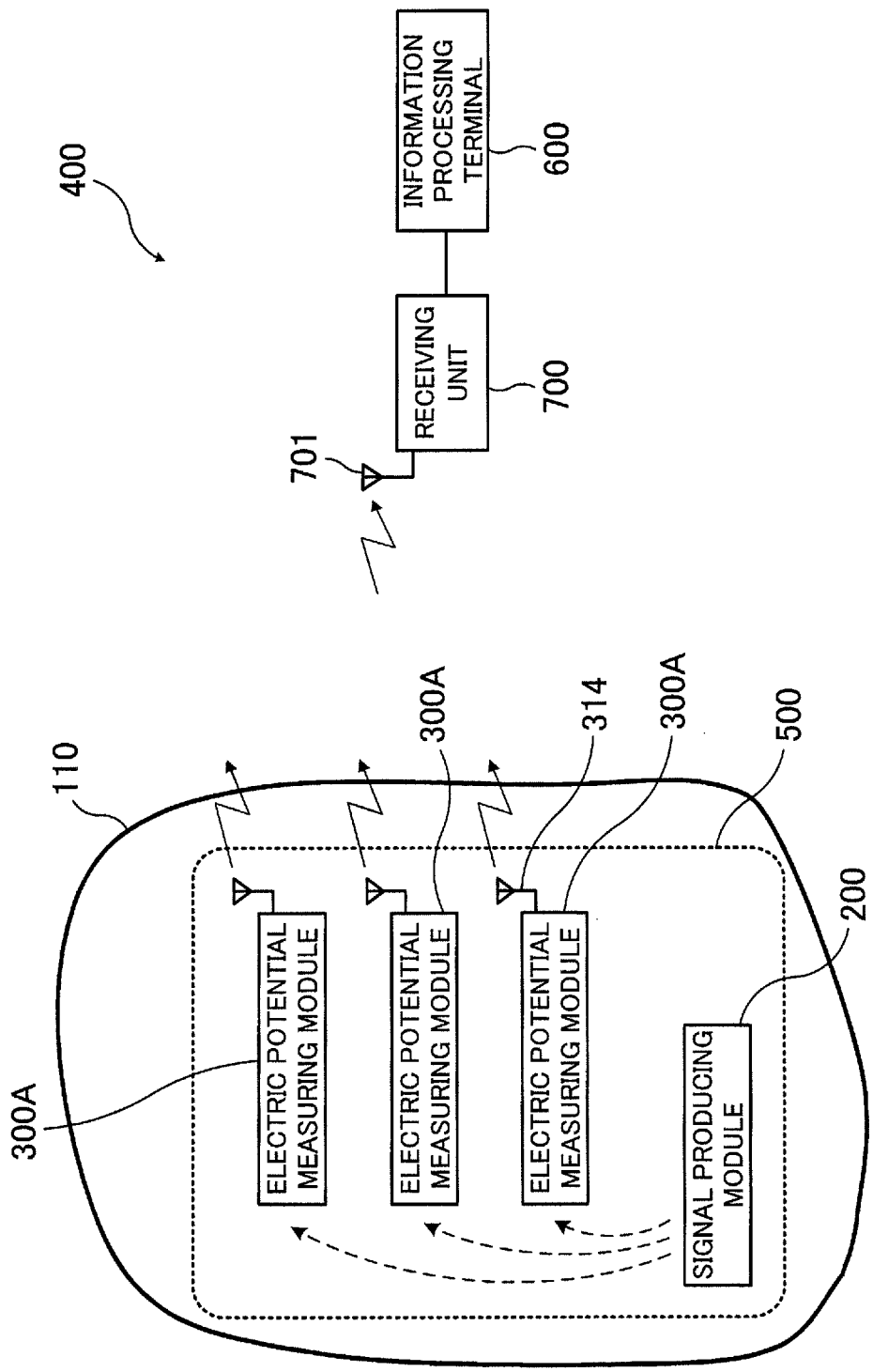
FIG. 8 illustrates an example of an electric potential measurement system which uses the electric potential measuring apparatus according to the first embodiment.

FIG. 8 illustrates an example of an electric potential measurement system which uses the electric potential measuring apparatus according to the first embodiment.

An electric potential measurement system 400 depicted in FIG. 8 includes an electric potential measuring apparatus 500, which is equipped with the signal producing module 200 and the electric potential measuring modules 300A, and an information processing terminal 600 such as a PC. FIG. 8 illustrates a case where the electric potential measuring apparatus 500 is equipped with one signal producing module 200 and three electric potential measuring modules 300A. Furthermore, FIG. 8 illustrates a case where the information processing terminal 600 is provided with a receiving unit 700 and an antenna 701.

One signal producing module 200 and three electric potential measuring modules 300A are placed on the measurement subject 110. Each electric potential measuring module 300A detects the signal which originates in the measurement subject 110 and the signal (indicated with chain line arrows in FIG. 8) which is supplied from the signal producing module 200 as described above. Each electric potential measuring module 300A measures the electric potential of the signal, which originates in the measurement subject 110, with reference to the electric potential of the reference signal obtained by averaging the signal supplied from the signal producing module 200. Then, each electric potential measuring module 300A sends information about the measured electric potential from the antenna 314.

All signals sent from the antenna 314 of the respective electric potential measuring modules 300A are received by the receiving unit 700 via the antenna 701. The receiving unit 700 is coupled via, for example, a USB (Universal Serial Bus) terminal, to the information processing terminal 600, so that data generated by the receiving unit 700 is sent to the information processing terminal 600. The data sent from the receiving unit 700 to the information processing terminal 600 is stored in a storage device contained in the information processing terminal 600 or a storage device coupled to the information processing terminal 600. The information processing terminal 600 executes analysis processing on distributions of the electric potentials in the measurement subject 110 and displays the analysis results on, for example, a monitor by using the data stored in the storage device as described above.

With the electric potential measuring apparatus according to the first embodiment as explained above, the signal supplied from the signal producing module 200 to the measurement subject 110, together with the signal which originates in the measurement subject 110, is detected by the electric potential measuring modules 300A placed at the measurement points on the measurement subject 110. Then, the reference signal is generated by averaging the signal supplied from the signal producing module 200; and the electric potential of the signal which originates in the measurement subject 110 is measured with reference to the electric potential of the reference signal.

With the electric potential measuring apparatus according to the first embodiment, the electric potentials at the measurement points where the electric potential measuring modules 300A are located are measured by placing the signal producing module 200 and the electric potential measuring modules 300A on the measurement subject 110. It is possible to place the signal producing module 200 and the electric potential measuring modules 300A at various positions on the measurement subject 110. Since there is a high degree of freedom with respect to the arrangement of the signal producing module 200 and the electric potential measuring modules 300A as mentioned above, they are applicable to various measurement subjects 110 such as animals, plants, ground surfaces, machinery, and equipment and are capable of measuring the electric potentials at various positions on the measurement subject 110.

Furthermore, the electric potential measuring module 300A may be placed on the measurement subject 110 without using wiring. Therefore, when measuring electric potential such as the electric potentials at a plurality of measurement points, it is possible to avoid burdensome work required, for example, to connect wires. Furthermore, when wiring is not used as mentioned above, it is possible to avoid a situation where electrodes or probes attached to the measurement subject 110 are pulled by the wiring, which hinders independent movement of the measurement subject 110.

As a result, the electric potential measuring apparatus according to the first embodiment is capable of easily measuring the electric potentials at various measurement points on various measurement subjects 110.

Next, a second embodiment will be explained.

Figure 9:
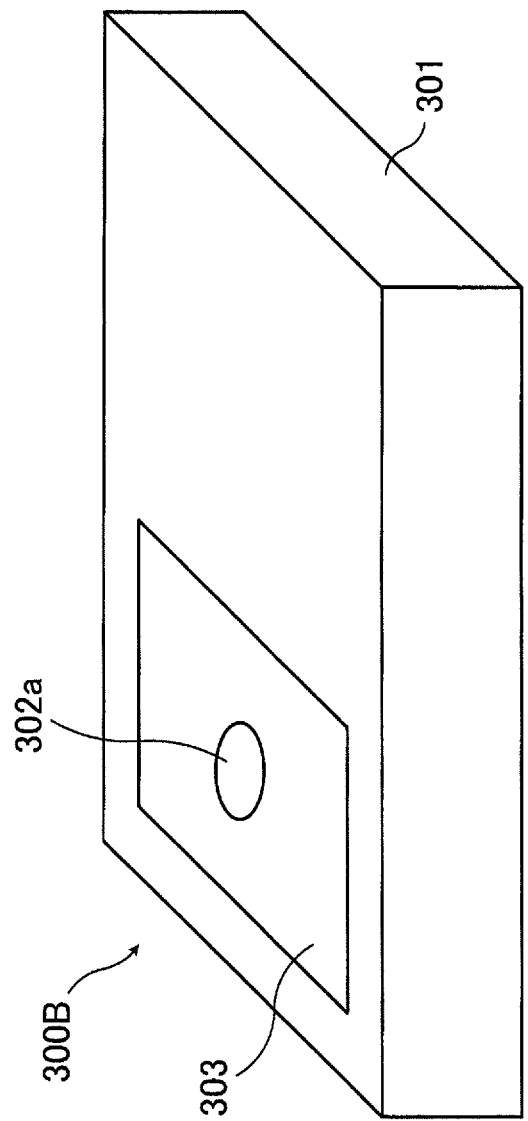
FIG. 9 illustrates an example of an electric potential measuring module according to a second embodiment.

FIG. 9 illustrates an example of an electric potential measuring module according to a second embodiment.

An electric potential measuring module 300B depicted in FIG. 9 includes a housing 301 and a single electrode 302a for detecting signals. An insulative adhesive material 303 is provided on the surface of the housing 301 where the electrode 302a is mounted, so that the electrode 302a is exposed. The difference between the electric potential measuring module 300B and the aforementioned electric potential measuring module 300A is that the electric potential measuring module 300B has such a single electrode 302a.

The electric potential measuring apparatus according to the second embodiment includes, for example, a plurality of such electric potential measuring modules 300B.

Figure 10:
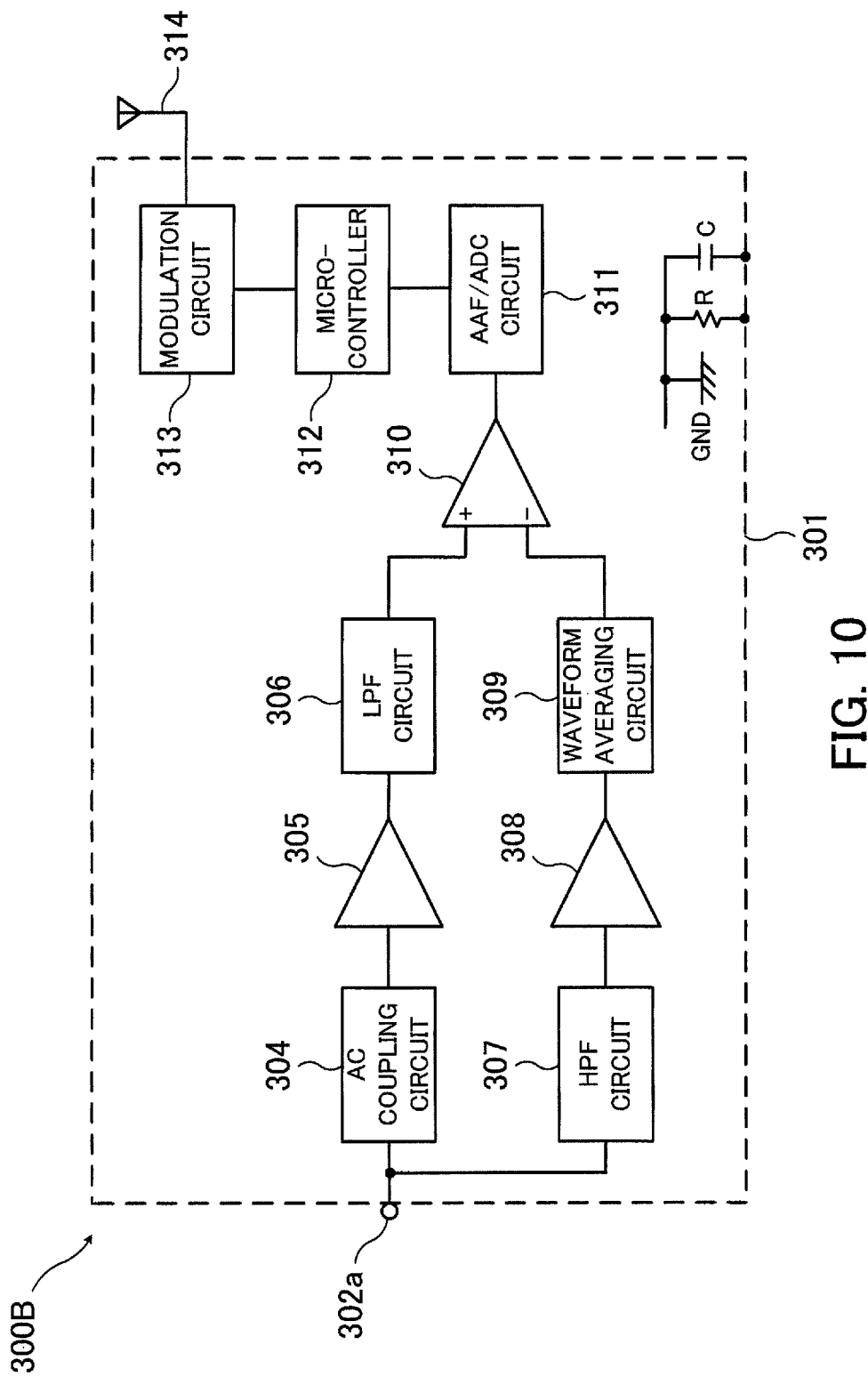
FIG. 10 illustrates a configuration example for an electric potential measuring module according to the second embodiment.

FIG. 10 illustrates a configuration example for an electric potential measuring module according to the second embodiment.

The electric potential measuring module 300B is configured as depicted in FIG. 10 so that a signal detected by the electrode 302a is split, and one split signal is input to the AC coupling circuit 304 and the other split signal is input to the HPF circuit 307. Other elements of the configuration are the same as those of the electric potential measuring module 300A described earlier.

The electric potential measuring module 300B is placed, together with the signal producing module 200, in the same manner as the electric potential measuring module 300A depicted in FIG. 4 so that its surface where the electrode 302a is mounted faces the surface of the measurement subject 110. The electric potential measuring module 300B is adhesively attached to the surface of the measurement subject 110 via the adhesive material 303 in FIG. 9, which is provided on the surface where the electrode 302a is mounted. Consequently, the electrode 302a comes into contact with the surface of the measurement subject 110 and the signal which propagates through the measurement subject 110 is detected by the electrode 302a. The electrode 302a detects a signal including both the signal supplied from the signal producing module 200 and the signal which originates in the measurement subject 100. The electric potential measuring module 300B measures the electric potential at the measurement point where the electric potential measuring module 300B is located, by using the detected signal and generates information about the electric potential.

The information generated by the electric potential measuring module 300B about the electric potential at the relevant measurement point is collected by, for example, the information processing terminal 600 in the same manner as in the electric potential measurement system 400 depicted in FIG. 8. Then, the information processing terminal 600 executes analysis processing on distributions of the electric potentials in the measurement subject 110 and displays the analysis results on, for example, the monitor.

As the single electrode 302a is made to come into contact with the measurement subject 110, the electric potential measuring module 300B detects signals from the measurement subject 110 and measures electric potential at a measurement point where the electric potential measuring module 300B is located. Therefore, it is possible to make the electrode 302a come into contact with the surface of the measurement subject 110 and detect the signals not only when the surface of the measurement subject 110 is relatively flat, but also even when the surface of the measurement subject 110 protrudes considerably with relatively large curvature.

The electric potential measuring apparatus equipped with the above-described electric potential measuring modules 300B is capable of easily measuring electric potentials at various measurement points on various measurement subjects 110.

Incidentally, the electric potential measuring modules 300A and 300B may be used together in addition to one signal producing module 200 in order to measure the electric potentials of the measurement subject 110. For example, the electric potential measuring module 300A equipped with the two electrodes 302a and 302b is placed at a measurement point on a relatively flat surface of the measurement subject 110 and the electric potential measuring module 300B equipped with the single electrode 302a is placed at a measurement point on a protruding surface with relatively large curvature of the measurement subject 110. Specifically speaking, the electric potential measuring module 300A is placed on the surface of the measurement subject 110 with which both the two electrodes 302a and 302b are capable of coming into contact; and the electric potential measuring module 300B is placed on the curved surface of the measurement subject 110 with which only the single electrode 302a is capable of coming into contact. Accordingly, either the electric potential measuring module 300A or the electric potential measuring module 300B may be selected to be used, depending on the shape of the surface where the relevant measurement point is located.

Next, a third embodiment will be explained.

Figure 11:
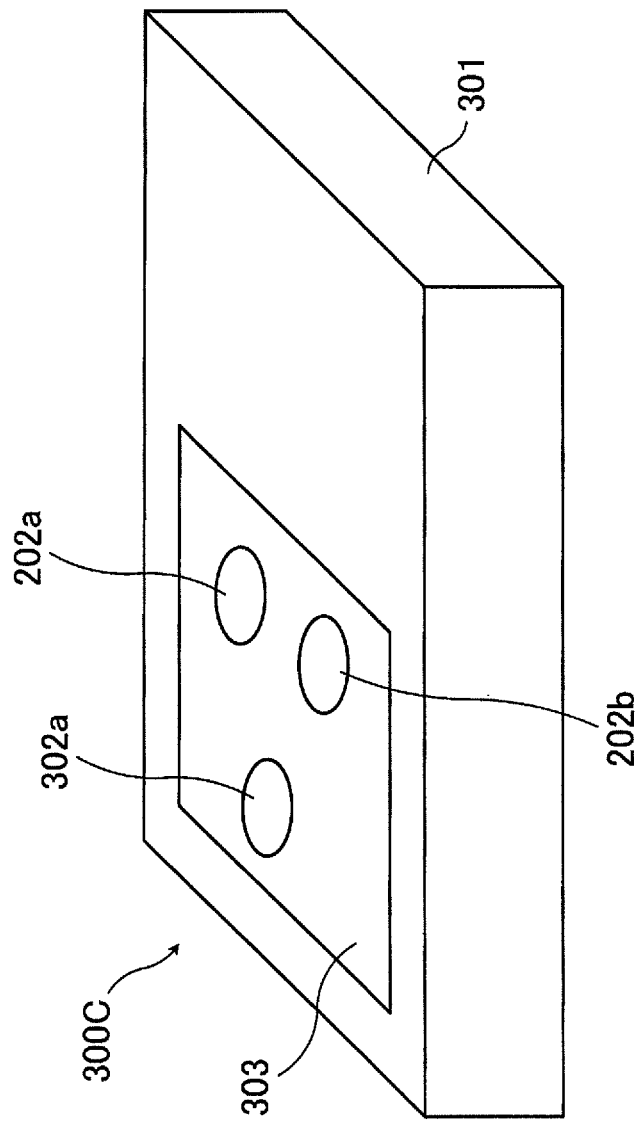
FIG. 11 illustrates an example of an electric potential measuring module according to a third embodiment.

FIG. 11 illustrates an example of an electric potential measuring module according to a third embodiment.

An electric potential measuring module 300C depicted in FIG. 11 includes a housing 301, a single electrode 302a for detecting signals, and two electrodes 202a and 202b for supplying signals. An insulative adhesive material 303 is provided on the surface of the housing 301 where the electrodes 302a, 202a and 202b are mounted, so that the electrodes 302a, 202a and 202b are exposed.

The electric potential measuring apparatus according to the third embodiment includes at least one such electric potential measuring module 300C, and the electric potential measuring module 300A or the electric potential measuring module 300B, or both of them. The electric potential measuring apparatus according to the third embodiment does not necessarily require the use of the aforementioned signal producing module 200. Incidentally, a case where the signal producing module 200 is not used will be taken and explained as an example below.

Figure 12:
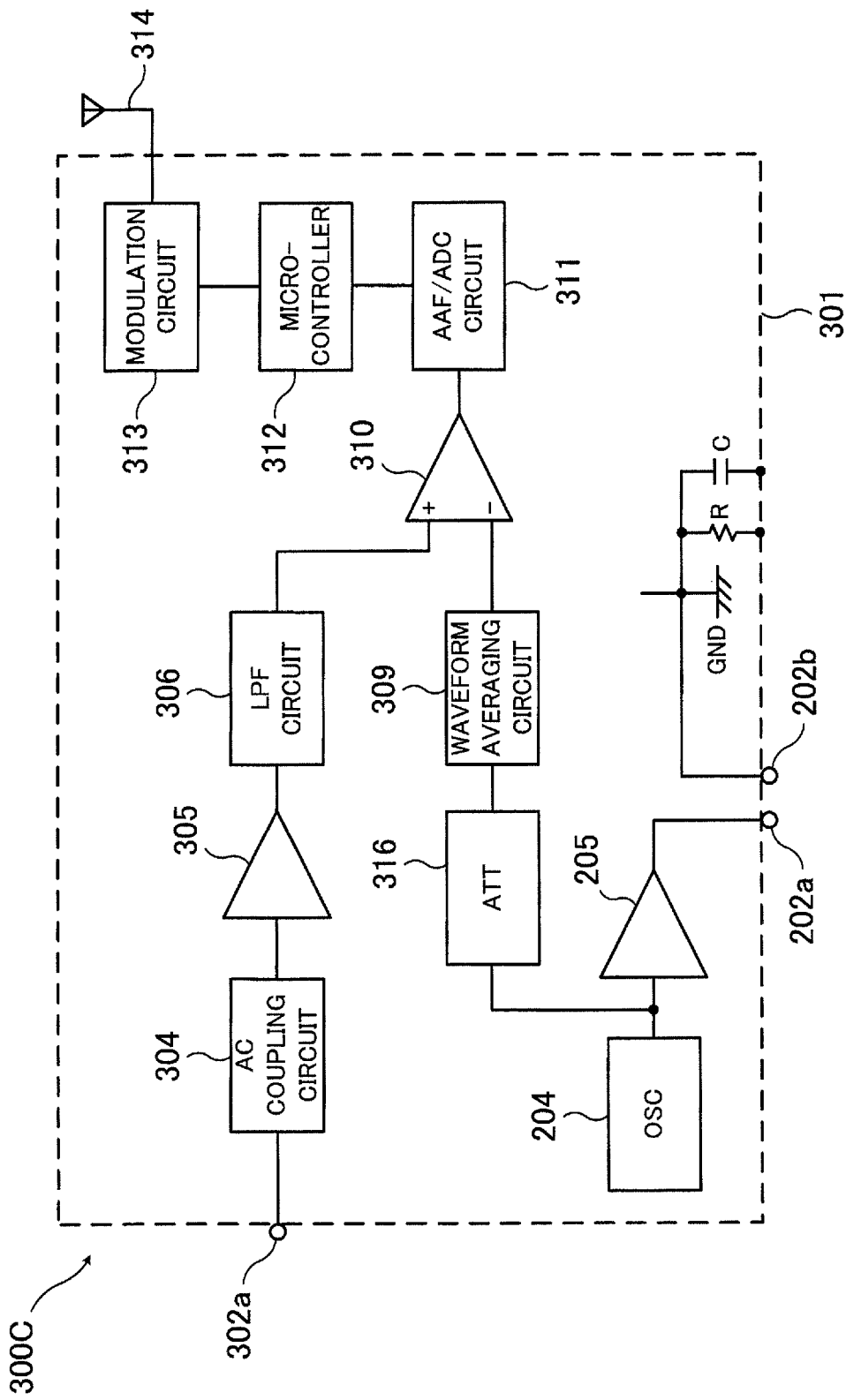
FIG. 12 illustrates a configuration example for the electric potential measuring module according to the third embodiment.

FIG. 12 illustrates a configuration example for an electric potential measuring module according to a third embodiment.

The electric potential measuring module 300C includes the oscillator (OSC) 204 as a producing unit, which produces the auxiliary signal, in the housing 301 as depicted in FIG. 12.

The signal oscillated by the oscillator 204 is split; one split signal is amplified by the amplifier 205 and the amplified signal is output from the electrode 202a. The electrode 202b serves as a ground (GND). When the electric potential measuring module 300C is placed on the measurement subject 110, the signal produced by the electric potential measuring module 300C is supplied and propagated to that measurement subject 110. Specifically speaking, this electric potential measuring module 300C serves in the role of the aforementioned signal producing module 200. Furthermore, the electric potential measuring module 3000 includes an attenuator (ATT) 316 which performs gain control on the other split signal oscillated by the oscillator 204. An output signal from the attenuator 316 is input to the waveform averaging circuit 309.

The electric potential measuring module 300C is placed, together with the electric potential measuring module 300A or the electric potential measuring module 300B, on the surface of the measurement subject 110 so that its surface where the electrodes 302a, 202a and 202b are mounted faces the surface of the measurement subject 110. The electric potential measuring module 300C is adhesively attached to the surface of the measurement subject 110 via the adhesive material 303 in FIG. 11.

Accordingly, the electrodes 302a, 202a, and 202b come into contact with the surface of the measurement subject 110 and the signal is supplied from the electrodes 202a and 202b to the measurement subject 110, and the signal which propagates through the measurement subject 110 is detected by the electrode 302a.

The electric potential measuring module 300A or the electric potential measuring module 300B, or both of them, may be placed on the measurement subject 110 as mentioned earlier. In that case, the electrodes 302a and 302b of the electric potential measuring module 300A and the electrode 302a of the electric potential measuring module 300B detect the signal supplied from the electric potential measuring module 300C and the signal which originates in the measurement subject 100. The signal detected by the electrodes 302a and 302b of the electric potential measuring module 300A is processed as described in the first embodiment; and as a result, electric potential at a measurement point where the electric potential measuring module 300A is located is measured and information about the electric potential is generated. The signals detected by the electrode 302a of the electric potential measuring module 300B are processed in the same manner; and electric potential at a measurement point where the electric potential measuring module 300B is located is measured and information about the electric potential is generated.

Similarly, the electrode 302a of the electric potential measuring module 300C placed on the measurement subject 110 detects the signal supplied from the electric potential measuring module 300C and the signal which originates in the measurement subject 100. The signal which originates in the measurement subject 100 is selected from the signal detected by the electrode 302a of the electric potential measuring module 300C as a result of the processing by the AC coupling circuit 304, the amplifier 305, and the LPF circuit 306; and the selected signal is input to the differential amplifier 310. Meanwhile, the signal which is oscillated by the oscillator 204 and then split undergoes gain control by the attenuator 316 and is then input to the waveform averaging circuit 309; and the averaged signal is input to the differential amplifier 310. As a result, the electric potential of the signal which has passed through the LPF circuit 306 (the signal which originates in the measurement subject 110) is obtained with reference to the electric potential of the reference signal averaged by the waveform averaging circuit 309; and the thus-obtained electric potential is amplified and output from the differential amplifier 310. In this way, the electric potential at the measurement point where the electric potential measuring module 300C is located is measured and information about the electric potential is generated.

The information generated by each electric potential measuring module 300A, 300B, and 300C about the electric potentials at the measurement points is collected by, for example, the information processing terminal 600 in the same manner as in the electric potential measurement system 400 depicted in FIG. 8. Then, the information processing terminal 600 executes analysis processing on distributions of the electric potentials in the measurement subject 110 and displays the analysis results on, for example, the monitor.

The electric potential measuring apparatus equipped with the above-described electric potential measuring module 300C is capable of easily measuring the electric potentials at various measurement points on various measurement subjects 110 without using the signal producing module 200. Incidentally, even when such an electric potential measuring module 300C is used, it is possible to use the signal producing module 200.

Next, a fourth embodiment will be explained.

Figure 13:
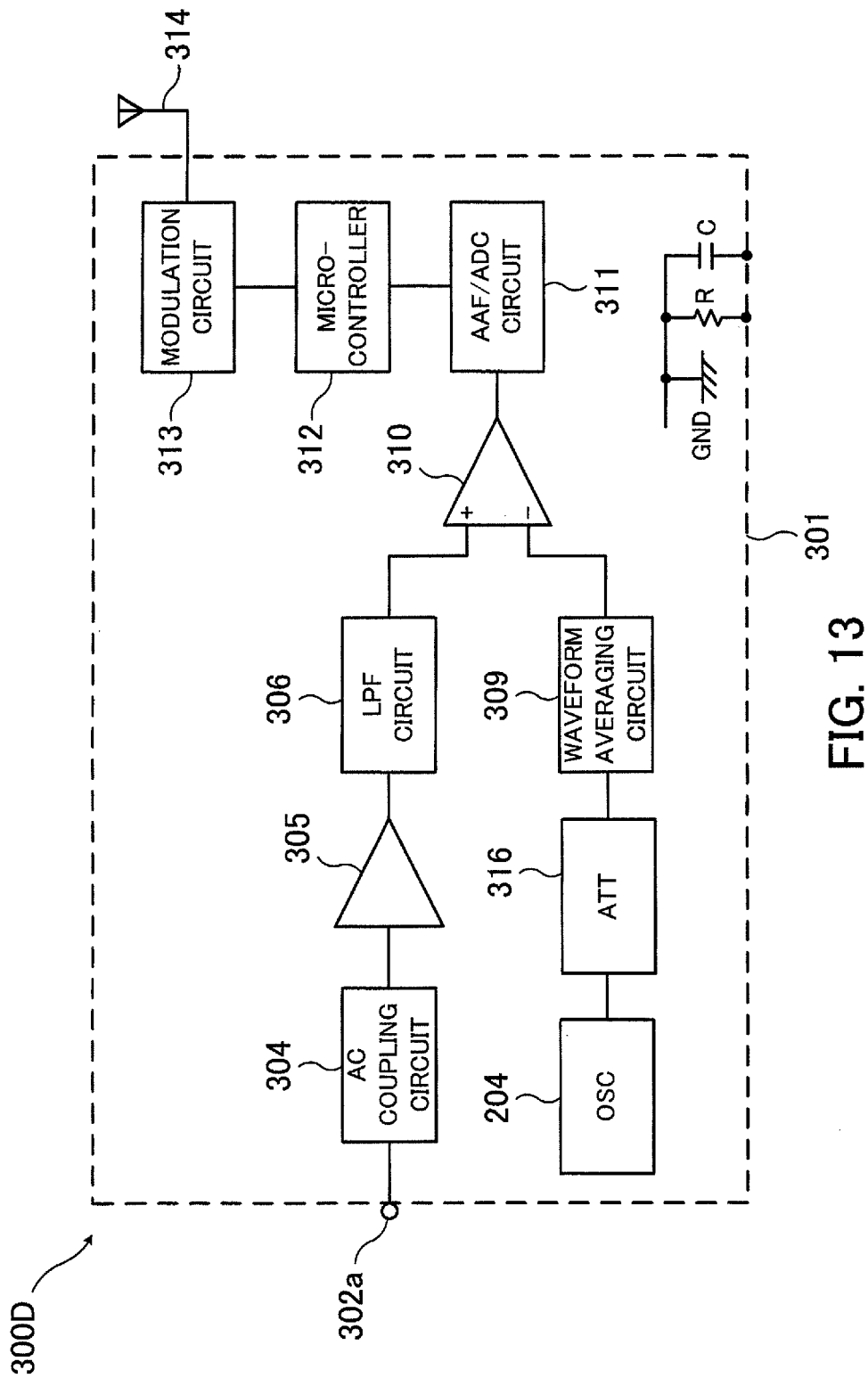
FIG. 13 illustrates a configuration example for an electric potential measuring module according to a fourth embodiment.

FIG. 13 illustrates a configuration example for an electric potential measuring module according to a fourth embodiment.

The difference between an electric potential measuring module 300D depicted in FIG. 13 and the aforementioned electric potential measuring module 300C is that the electric potential measuring module 300D is designed to input a signal from the oscillator 204 provided therein to an attenuator 316 without allowing the signal to split. With the electric potential measuring module 300D, the signal oscillated by the oscillator 204 is not supplied to the measurement subject 110, but is directly used to generate a reference signal to be input to the differential amplifier 310.

The electric potential measuring apparatus according to the fourth embodiment includes, for example, a plurality of such electric potential measuring modules 300D. Information generated by the electric potential measuring module 300D about electric potentials at measurement points is collected by, for example, the information processing terminal 600 in the same manner as in the electric potential measurement system 400 depicted in FIG. 8. Then, the information processing terminal 600 executes analysis processing on distributions of the electric potentials in the measurement subject 110 and displays the analysis results on, for example, the monitor.

The electric potential measuring apparatus equipped with the above-described electric potential measuring modules 300D is capable of generating the reference signal within the individual electric potential measuring modules 300D and measuring the electric potentials at the measurement points where the electric potential measuring modules 300D are located, without supplying a signal to generate the reference signal to the measurement body 110. Such an electric potential measuring apparatus is capable of easily measuring the electric potentials at various measurement points on various measurement subjects 110.

Next, a fifth embodiment will be explained.

Figure 14:
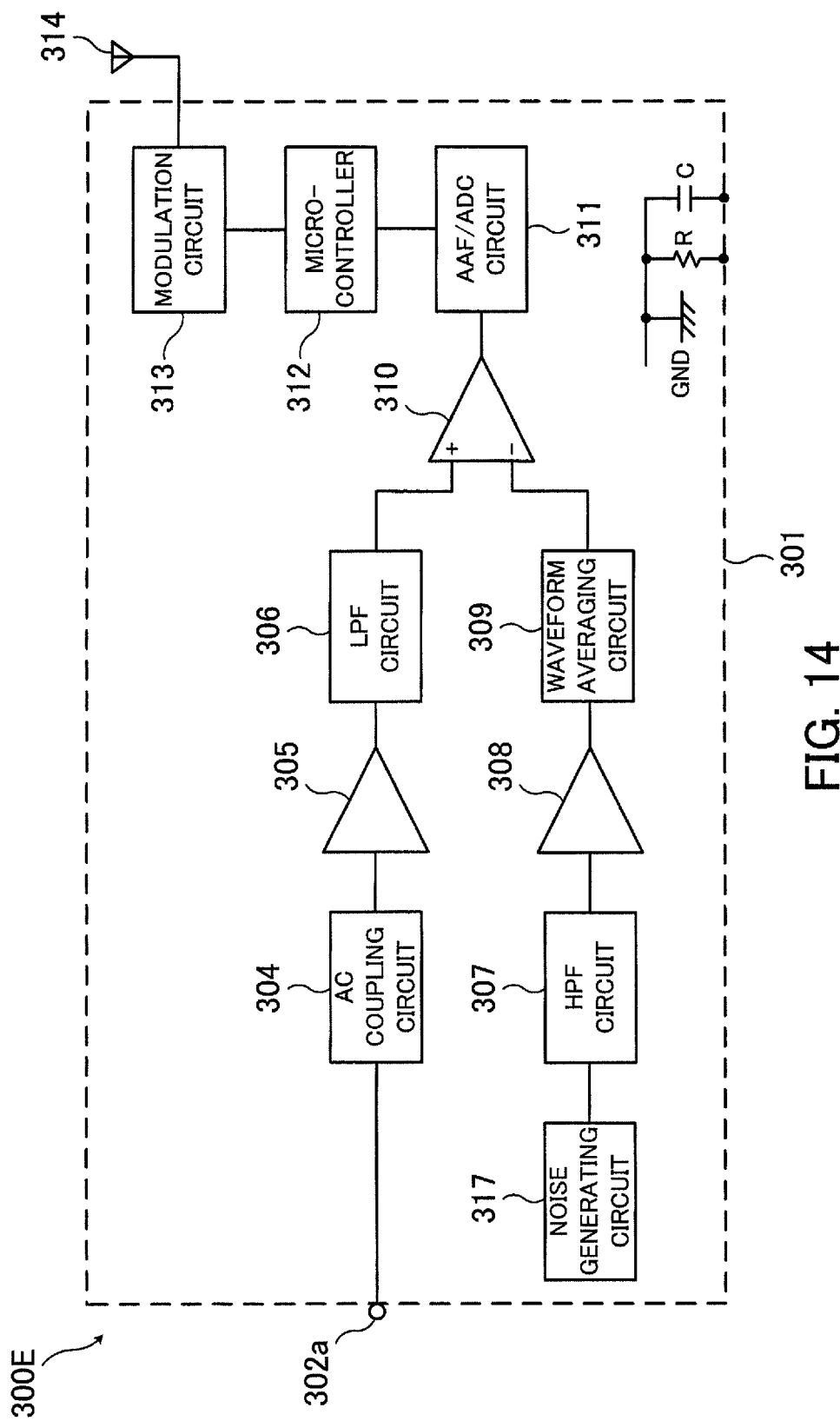
FIG. 14 illustrates a configuration example for an electric potential measuring module according to a fifth embodiment.

FIG. 14 illustrates a configuration example for an electric potential measuring module according to a fifth embodiment.

An electric potential measuring module 300E depicted in FIG. 14 includes a noise generating circuit 317. It is possible to use, for example, resistors and noise diodes for the noise generating circuit 317. The electric potential measuring module 300E is designed so that a noise signal generated by the noise generating circuit 317 is input to the HPF circuit 307. The noise signal generated by the noise generating circuit 317 will not be supplied to the measurement subject 110. The electric potential measuring module 300E uses the noise signal generated by the noise generating circuit 317 to generate the reference signal to be input to the differential amplifier 310.

The electric potential measuring apparatus according to the fifth embodiment includes, for example, a plurality of such electric potential measuring modules 300E. Information generated by the electric potential measuring modules 300E about electric potentials at measurement points is collected by, for example, the information processing terminal 600 in the same manner as in the electric potential measurement system 400 depicted in FIG. 8. Then, the information processing terminal 600 executes analysis processing on distributions of the electric potentials in the measurement subject 110 and displays the analysis results on, for example, the monitor.

The electric potential measuring apparatus equipped with the above-described electric potential measuring modules 300E generates a stable reference signal within the individual electric potential measuring modules 300E and measures the electric potentials at the measurement points where the electric potential measuring modules 300E are located, without supplying the signal to generate the reference signal to the measurement body 110. Such an electric potential measuring apparatus is capable of easily and properly measuring the electric potentials at various measurement points on various measurement subjects 110.

The electric potential measuring apparatuses according to the first to fifth embodiments have been described above. The information obtained by the electric potential measuring apparatus about the electric potentials of the measurement subject 110 is collected and processed by the information processing terminal.

Subsequently, data processing by such an information processing terminal will be explained as a sixth embodiment. Here, the information processing terminal 600 where the receiving unit 700 and the antenna 701 are provided as depicted in FIG. 8 will be taken and explained as an example.

Figure 15:
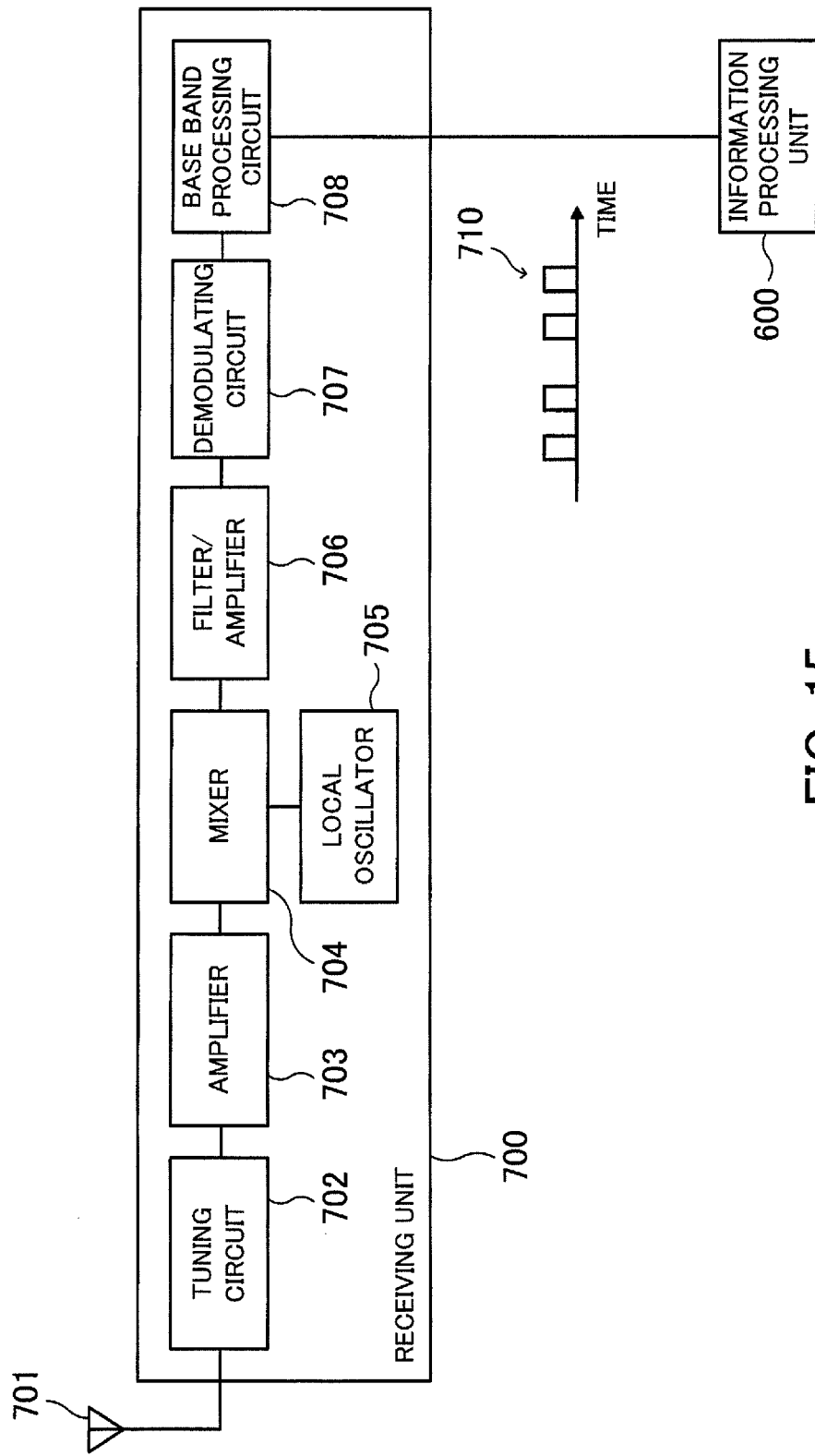
FIG. 15 is an explanatory diagram illustrating an example of an information processing unit equipped with a receiving unit and an antenna.
Figure 16:
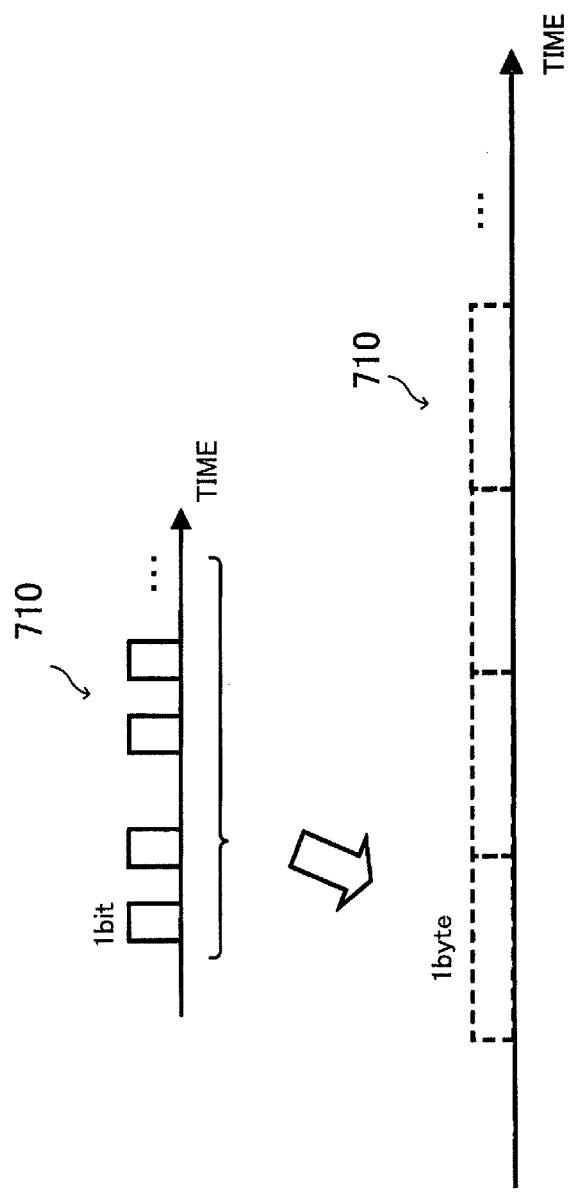
FIG. 16 is an explanatory diagram (1) of an example of processing by the information processing terminal.
Figure 17:
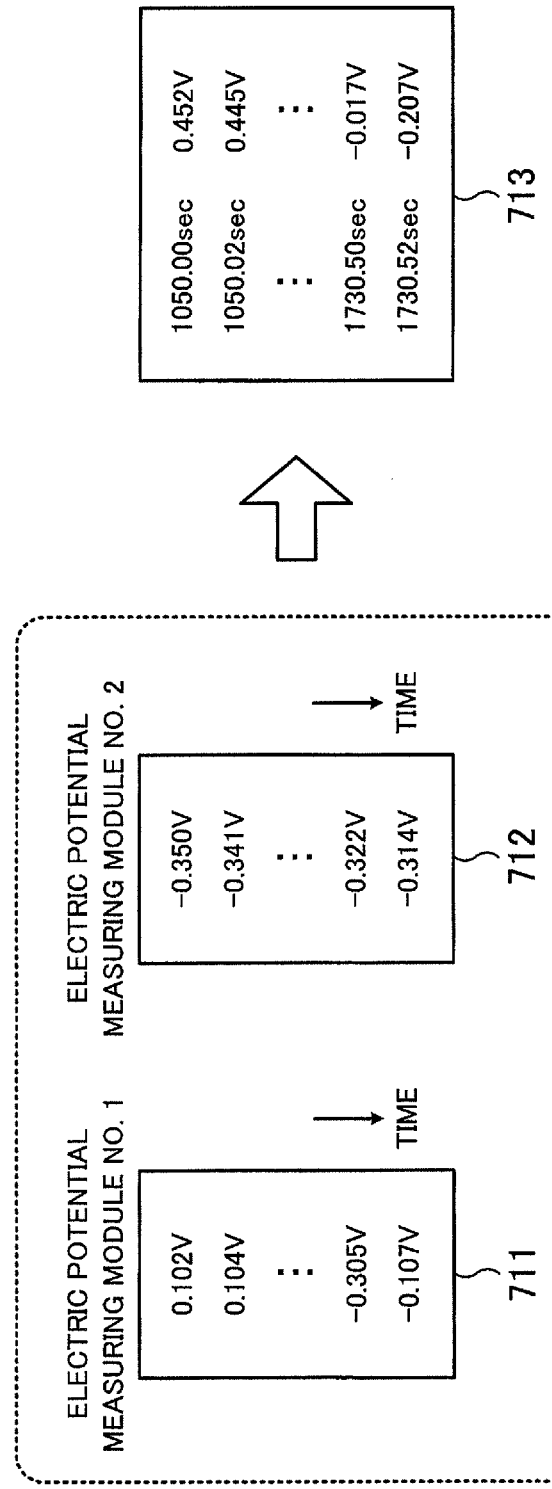
FIG. 17 is an explanatory diagram (2) of an example of processing by the information processing terminal.

FIG. 15 is an explanatory diagram illustrating examples of an information processing unit equipped with a receiving unit and an antenna. FIG. 16 and FIG. 17 are explanatory diagrams illustrating an example of processing by the information processing terminal.

A signal which is generated by each electric potential measuring module (electric potential measuring modules 300A, 300B, 300C, 300D, and 300E) placed on the measurement subject and includes information about the electric potential is sent from its antenna (antenna 314). The signal sent from the antenna is received by the antenna 701 and the receiving unit 700 at the information processing terminal 600 as depicted in FIG. 15.

The receiving unit 700 includes, for example, a tuning circuit 702, an amplifier 703, a mixer 704, a local oscillator 705, a filter/amplifier 706, a demodulation circuit 707, and a base band processing circuit 708 as depicted in FIG. 15.

In this circumstance, the tuning circuit 702 selects a signal of a target frequency from signals received by the antenna 701. The amplifier 703 amplifies the output signal from the tuning circuit 702. The mixer 704 converts the frequency of the output signal from the amplifier 703 (conversion to an IF [Intermediate Frequency]). The local oscillator 705 supplies a signal of a target frequency, which is to be used for the frequency conversion by the mixer 704, to the mixer 704. The filter/amplifier 706 has its filter circuit allow a signal of frequencies within a specified range centered on the intermediate frequency to pass and has its amplifier amplify that signal. The demodulation circuit 707 performs demodulation by using the output signal from the filter/amplifier 706. The base band processing circuit 708 executes specified base band processing.

As a result of the processing executed by such a receiving unit 700 on the signal received by the antenna 701, a pulse train 710 of a digital signal (bit signal) as depicted in FIG. 15 and FIG. 16 is generated and is sent via, for example, a USB terminal, to the information processing terminal 600. For example, the ASCII (American Standard Code for Information Interchange) code is used for data of the pulse train 710. An address is assigned in advance to each electric potential measuring module placed on the measurement subject and that address is expressed with binary codes (hexa codes) and included in the data of the pulse train 710. Furthermore, the data of the pulse train 710 includes various control codes (such as a header and End Of File [EOF]).

With the information processing terminal 600, information about the electric potentials, which is sent from each electric potential measuring module (in this example, from two electric potential measuring modules No. 1 and No. 2), is extracted chronologically from the pulse train 710 sent from the receiving unit 700. For example, the information is extracted 50 times per second from each electric potential measuring module No. 1 or No. 2. FIG. 17 illustrates an example of the extracted data from each of the electric potential measuring modules No. 1 and No. 2 (extracted data 711 and 712). Electric potential values in the extracted data 711 and 712 are values of the electric potentials measured by each electric potential measuring module No. 1 or No. 2 with reference to the electric potential of the reference signal averaged as explained earlier.

At the same time the chronological acquisition of the electric potentials like the extracted data 711 and 712 takes place, the information processing terminal 600 calculates the difference between the electric potentials of the electric potential measuring modules No. 1 and No. 2 at each point in time. Then, the information processing terminal 600 collects the time and the calculation results of the electric potential differences, as table data in, for example, Comma Separated Values [CSV] format, in the storage device. FIG. 17 illustrates an example of the obtained table data (table data 713).

The information processing terminal 600 displays table data, which have been sequentially accumulated in the storage device, or table data in the storage device, which have been obtained within the entire measurement time, as numeric values or graphs on the display device such as the monitor. As a result of such processing, chronological changes of the electric potential differences between the measurement points where the electric potential measuring modules No. 1 and No. 2 are located are obtained.

Incidentally, when data are encrypted (for example, Advanced Encryption Standard [AES] encryption) or encoded (for example, Manchester coding), the information processing terminal 600 also executes decrypting/decoding processing on the encrypted or encoded data.

It is possible to use a computer such as a PC as the information processing terminal 600.

Figure 18:
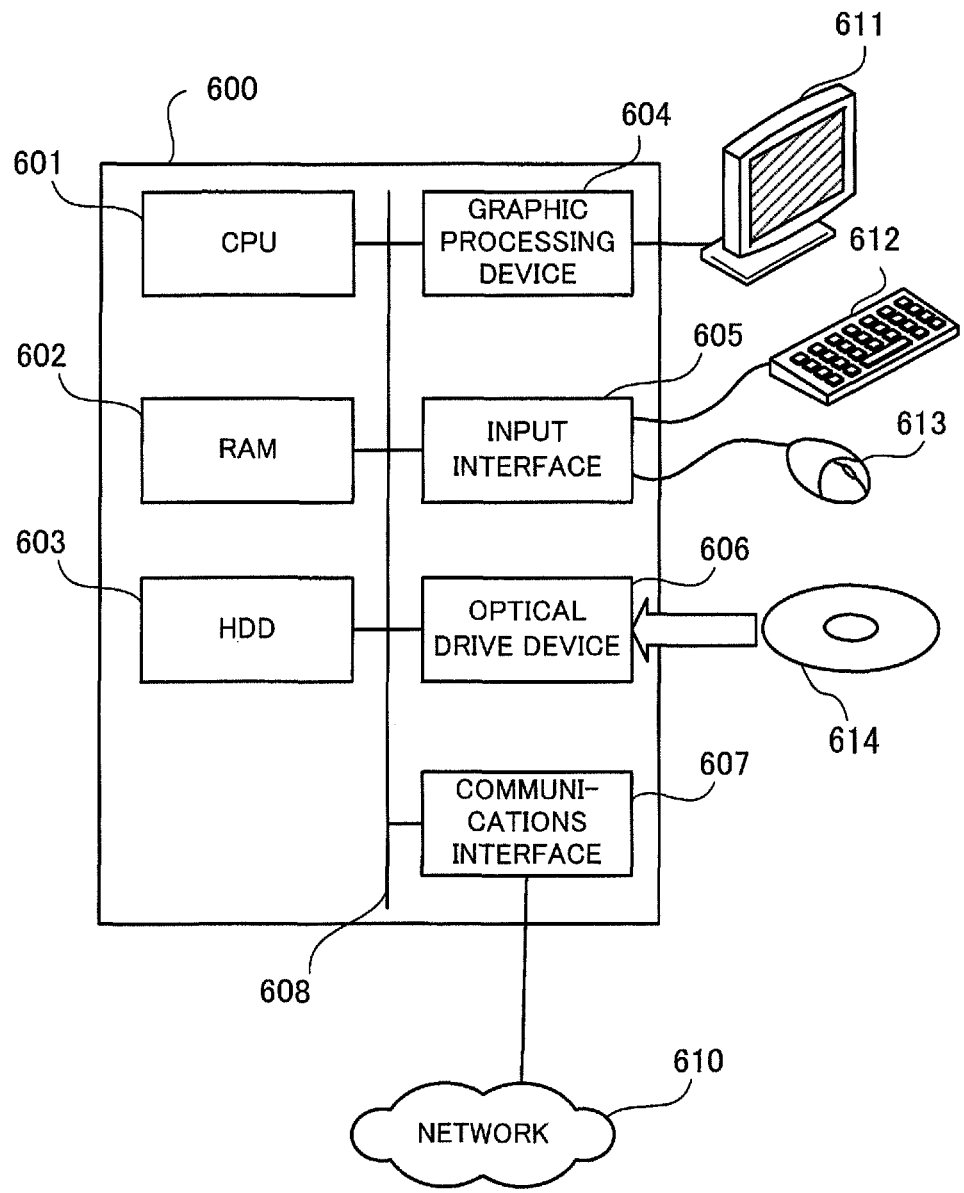
FIG. 18 illustrates a hardware configuration example for the information processing terminal.

FIG. 18 illustrates a hardware configuration example for the information processing terminal.

The entire information processing terminal 600 is controlled by a Central Processing Unit (CPU) 601. A Random Access Memory (RAM) 602 which is coupled via a bus 608 to the CPU 601 stores Operating System (OS) programs and application programs to be executed by the CPU 601, and various data required for processing by the CPU 601.

Peripheral equipment coupled to the bus 608 includes a hard disk drive (HDD) 603, a graphic processing device 604, an input interface 605, an optical drive device 606, and a communications interface 607.

The HDD 603 stores OS programs, application programs, and various data. The graphic processing device 604 displays images on a screen of a monitor 611 for, for example, a display device using a Cathode Ray Tube (CRT) or a liquid crystal display in accordance with commands from the CPU 601. The input interface 605 sends signals, which are sent from a keyboard 612 and a mouse 613, to the CPU 601. The optical drive device 606 reads data recorded on an optical disc 614 such as a Digital Versatile Disc (DVD) or a Compact Disc Read Only Memory (CD-ROM). The communications interface 607 sends and receives data to and from other computers or communication equipment via a network 610.

The above-described hardware configuration makes it possible to implement processing functions of the information processing terminal 600.

The above-described processing functions are implemented by a computer, and programs in which the processing content of the functions to be implemented by the information processing terminal 600 is described are provided. The above-described processing functions are implemented on the computer by execution of the programs by the computer. It is possible to record the programs with the processing content described therein on computer-readable storage media such as magnetic storage devices, optical discs, magneto-optical storage media, or semiconductor memories.

The electric potential measuring apparatus equipped with the signal producing module and the electric potential measuring module, and the electric potential measurement system using the electric potential measuring apparatus have been described. The electric potential measuring apparatus and electric potential measurement system described above are capable of easily measuring the electric potentials at various measurement points on various measurement subjects.

Incidentally, it is possible to provide the signal producing module and electric potential measuring module, which are included in the electric potential measuring apparatus, with elements for converting, for example, heat, vibrations, and light to electric power, and to use energy, which is generated by those elements, as a power source, that is, so-called harvesting power supply.

The disclosed electric potential measuring apparatus is capable of easily and properly measuring the electric potentials of signals at various measurement points on various measurement subjects.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that various changes, substitutions, and alterations could be made hereto without departing from the spirit and scope of the invention.

What is claimed is:

1. An electric potential measuring apparatus comprising:
   a first module; and
   a second module which is a module separate from the first module; wherein
   the first module includes:
      a detecting unit configured to detect a second signal including a first signal from a measurement subject by contacting a surface of the measurement subject, the first signal being an electric potential measurement target signal within a first frequency range, which propagates through the measurement subject;
      a generating unit configured to generate a fourth signal by averaging a third signal within a second frequency range which is different from the first frequency range; and
      a measuring unit for measuring an electric potential of the first signal with reference to an electric potential of the fourth signal;
   the second module includes a producing unit configured to produce the third signal and supplies the third signal to the measurement subject;
   the first module has the detecting unit detect the second signal including the first signal and the third signal and has the generating unit generate the fourth signal by averaging the third signal included in the detected second signal;
   the detecting unit includes a first electrode and a second electrode that detect the second signal;
   the generating unit generates the fourth signal by averaging the third signal included in the second signal detected by the first electrode; and
   the measuring unit measures the electric potential of the first signal included in the second signal detected by the second electrode.

2. The electric potential measuring apparatus according to claim 1, wherein the first module is provided in plurality.

3. The electric potential measuring apparatus according to claim 1, wherein the first module includes a first housing, which accommodates the generating unit and the measuring unit, and the detecting unit is provided on a surface of the first housing; and
   wherein the second module includes a second housing, which accommodates the producing unit, and a supply unit configured to supply the third signal produced by the producing unit to the measurement subject is provided on a surface of the second housing.

4. The electric potential measuring apparatus according to claim 3, wherein an adhesive part that is adhesively attachable to the measurement subject is provided on the surface of the first housing where the detecting unit is placed, and on the surface of the second housing where the supply unit is placed.

5. An electric potential measuring apparatus comprising:
   a first module including:
      a first detecting unit configured to detect a second signal including a first signal from a measurement subject by contacting a surface of the measurement subject, the first signal being an electric potential measurement target signal within a first frequency range, which propagates through the measurement subject;
      a first generating unit configured to generate a fourth signal by averaging a third signal within a second frequency range which is different from the first frequency range;
      a first measuring unit for measuring an electric potential of the first signal with reference to an electric potential of the fourth signal; and
   a producing unit configured to produce the third signal;
   wherein the first module has the first generating unit generate the fourth signal by averaging the third signal produced by the producing unit.

6. The electric potential measuring apparatus according to claim 5, further comprising:
   the first module; and
   a second module including:
      a second detecting unit configured to detect the second signal including the first signal from the measurement subject by contacting the surface of the measurement subject;
      a second generating unit configured to generate the fourth signal by averaging the third signal produced by the first module; and
      a second measuring unit configured to measure the electric potential of the first signal, which is included in the second signal detected by the second detecting unit, with reference to the electric potential of the fourth signal generated by the second generating unit.

7. The electric potential measuring apparatus according to claim 6, wherein the second module is provided in plurality.

8. The electric potential measuring apparatus according to claim 5, wherein the first module includes a housing, which accommodates the first detecting unit, the first generating unit, the first measuring unit, and the producing unit, and a supply unit configured to supply the third signal produced by the producing unit to the measurement subject is provided on a surface of the housing.

9. The electric potential measuring apparatus according to claim 8, wherein an adhesive part that is adhesively attachable to the measurement subject is provided on the surface of the housing where the supply unit is placed.

10. The electric potential measuring apparatus according to claim 5, wherein the producing unit is an oscillating circuit.

11. The electric potential measuring apparatus according to claim 1, further comprising a transmission unit designed to wirelessly send information about the electric potential measured by the measuring unit to an information processing terminal.

12. The electric potential measuring apparatus according to claim 5, further comprising a transmission unit designed to wirelessly send information about the electric potential measured by the first measuring unit to an information processing terminal.

* * * * *